United States Patent [19]
Mehra

[11] Patent Number: 5,546,764
[45] Date of Patent: Aug. 20, 1996

[54] ABSORPTION PROCESS FOR RECOVERING ETHYLENE AND HYDROGEN FROM REFINERY AND PETROCHEMICAL PLANT OFF-GASES

[75] Inventor: Yuv R. Mehra, The Woodlands, Tex.

[73] Assignee: Advanced Extraction Technologies, Inc., Houston, Tex.

[21] Appl. No.: 398,554

[22] Filed: Mar. 3, 1995

[51] Int. Cl.$^6$ .................................. F25J 3/00; C07C 7/00
[52] U.S. Cl. ................................................. 62/625; 62/938
[58] Field of Search ...................................... 62/17, 11, 20

[56] References Cited

U.S. PATENT DOCUMENTS

| | | |
|---|---|---|
| 4,035,167 | 7/1977 | Starks . |
| 4,740,222 | 4/1988 | Mehra . |
| 4,743,282 | 5/1988 | Mehra ........................ 62/17 |
| 4,832,718 | 5/1989 | Mehra . |
| 5,019,143 | 5/1991 | Mehra . |
| 5,220,097 | 6/1993 | Lam et al. . |
| 5,326,929 | 7/1994 | Mehra et al. . |
| 5,462,583 | 10/1995 | Wood et al. . |

FOREIGN PATENT DOCUMENTS

4217611A1  12/1993  Germany .

OTHER PUBLICATIONS

Bauer, "Safe Ethylene Recovery from FCC Off–Gas Streams," Prepared for Presentation at AIChE 1994 Spring National Meeting, Atlanta, Georgia (Apr. 17–21, 1994).

Mehra, "Can We Really Afford to Keep Burning Light Olefins and Hydrogen in our Refineries?," CMAI Seminar, Houston, Texas (Mar. 24–25, 1993), pp. 1–10.

Mehra, "Processing Hydrocarbon Gases with the Mehra Process$^{SM}$ Technology," Chemical Engineering (Oct. 27, 1986), Houston, Texas.

Fair et al., "Ethylene Purification—Demethanization," Chemical Eng. Progress, vol. 54, No. 12 (Dec. 1958), pp. 39–47.

*Primary Examiner*—Christopher B. Kilner
*Attorney, Agent, or Firm*—Arnold, White & Durkee

[57] ABSTRACT

An absorption process for recovering hydrogen, ethylene, methane and heavy hydrocarbons from refinery and petrochemical off-gas streams wherein the absorption solvent is comprised of heavy hydrocarbons derived from the off-gas feed stream; no external solvent is used. The process comprises the steps of absorbing ethylene out of the feed off-gas in an absorber stripper using the absorption solvent, and fractionating the rich absorption solvent in a distillation column to produce an ethylene product stream as the overhead stream and the heavy hydrocarbon absorption solvent as the bottoms stream.

21 Claims, 4 Drawing Sheets

ABSORPTION PROCESS FOR RECOVERING ETHYLENE AND HYDROGEN FROM REFINERY AND PETROCHEMICAL PLANT OFF-GASES

FIELD OF THE INVENTION

This invention relates to physical absorption processes for recovering ethylene and associated hydrogen from refinery and petrochemical plant off-gas streams.

BACKGROUND OF THE INVENTION

Currently, it is the usual practice to burn refinery and petrochemical off-gas streams containing ethylene in flare stacks or as fuel even though the fuel gas value of the streams is significantly less than the product value of the recoverable ethylene. The high cost of producing ethylene by thermal cracking of hydrocarbon feedstocks, which is the primary production route to ethylene, should motivate ethylene consumers to recover ethylene from off-gas streams that are emitted in their complexes before opting to build or expand thermal cracking units or to purchase makeup ethylene. Recovery of ethylene from refinery off-gas streams is particularly feasible at the many sites where the off-gas streams are near an ethylene plant because the recovered ethylene stream can conveniently be purified in towers already operating in the ethylene plant.

The principal ethylene bearing off-gas streams are from fluid catalytic cracking (FCC) units and delayed cokers. A typical fluid catalytic cracker unit emits between about 20,000 to 30,000 tons per year of ethylene in off-gas streams. In North America, fluid catalytic cracker units alone produce about 6,000 MM lbs/Yr of ethylene and about 500 MMSCFD of hydrogen which are potentially recoverable.

Demand in refining and petrochemical operations for hydrogen to desulfurize feedstocks and liquid heavy fractions is increasing because sulfur in crude solvents now being refined is increasing and more heavy crudes with higher carbon-to-hydrogen ratio are being produced. It is estimated that petroleum refineries and petrochemical plants in North America are burning off-gases containing 1,500 to 2,000 million cubic feet per day of recoverable hydrogen. Paradoxically, the hydrogen in these streams is not recovered; the streams are burned in flare stacks, vented to the atmosphere or burned as fuel in fuel gas. Most of the chemical hydrogen used in refineries and chemical plants is made on purpose at substantial cost by steam reforming or partially oxidizing methane and other hydrocarbons followed by purification in pressure swing adsorption units and membrane diffusion units.

Table 1 presents a range of compositions of typical ethylene bearing off-gas streams.

TABLE 1

| Component | Volume % |
| --- | --- |
| $H_2$ | 7–48 |
| $N_2$ | 0–12 |
| $CH_4$ | 15–58 |
| $C_2H_4$ | 2–15 |
| $C_2H_6$ | 2–25 |
| $C_{3+}$ | 2–15 |

Ethylene bearing off-gases usually contain methane and often also hydrogen in economically recoverable quantities. Ethylene bearing refinery and petrochemical off-gas streams also contain varying amounts of heavy hydrocarbons in the C4 to C10 range which can include alkanes, olefins and aromatics. Small amounts of water, nitrogen oxides, carbon monoxide, carbon dioxide, acetylene, methylacetylene, propadiene, butenes, and higher hydrocarbons are typically also found in ethylene bearing off-gases.

Why don't operators recover ethylene and associated hydrogen from off-gas streams? The answer is that it costs more to recover ethylene and hydrogen using the cryogenic recovery technology and processes than to purchase or produce the makeup ethylene. Even adding in the chemical value of associated hydrogen, which is two to three times its fuel value, does not make recovering ethylene from off-gas streams using cryogenic technology cost effective. Moreover, cryogenic processes are not flexible and do not adapt well to changes in feed composition and feed gas flow rates that are endemic to refinery and petrochemical off-gas streams, so that while cryogenic recovery is technically feasible, it is impractical in most applications. Another consideration is that several devastating explosions in cryogenic ethylene recovery units have been attributed to formation of explosive compounds from nitrogen oxide, which are found in most off-gas streams, at the very low temperatures encountered in cryogenic units.

For the foregoing reasons, there is need for a cost effective, flexible and safe process for recovering ethylene and associated hydrogen from refinery and petrochemical off-gas stream.

The solution lies in Mehra processes which are absorption processes that utilize a physical absorption solvent to separate and recover hydrogen, methane, ethylene and other valuable hydrocarbons from mixed hydrocarbon streams. Mehra technology has been applied to recover ethylene, hydrogen and methane from refinery and petrochemical off-gas streams and to reject nitrogen from natural gas. Generally, Mehra processes compete with cryogenic processes in these applications. Depending on the application, Mehra specifies absorption solvents that are selected from preferred groups and processed designs which optimally synergize solvent with process. Among the preferred Mehra solvents are C4 to C10 hydrocarbons, including paraffins, naphthenes and aromatics. Mehra technology is described in U.S. Pat. Nos. 4,832,718, 4,740,222, 5,019,143, 5,220,097 and 5,326,929, which are incorporated herein by reference.

In general, Mehra processes operate at a higher temperature than cryogenic processes which provide advantages over cryogenic processes: 1) exotic cryogenic construction materials required to withstand cryogenic temperatures are not required in Mehra processes; 2) feed purification specifications are more relaxed; 3) cryogenic processes are intensively heat integrated to reduce energy consumption whereas Mehra processes are not. Accordingly, Mehra processes are more flexible and adaptable to changes. Process conditions can be changed quickly "on-line" with no adverse impact on operability and without equipment modifications to alter product stream compositions or maintain product composition should feed composition change.

While the Mehra technology has provided many advances over the cryogenic processes, there continually exists a need to refine the processes to attain more efficient and cost effective measures.

SUMMARY OF THE INVENTION

The present invention is directed to a process for treating a refinery or chemical plant off-gas stream that contains hydrogen, methane, ethylene and heavy hydrocarbons to separate and recover ethylene and associated hydrogen, methane and heavy hydrocarbons, using Mehra physical absorption technology.

The process of the present invention advantageously includes the steps of:

(a) continuously and countercurrently contacting the feed gas stream with an absorption solvent stream in an absorber stripper to produce an absorber overhead gas stream comprised of hydrogen and methane and a bottoms liquid stream comprised of the absorption solvent and absorbed ethylene and heavy hydrocarbons;

(b) fractionating the absorption bottoms stream in an ethylene distillation column to produce an overhead stream comprising ethylene and heavy hydrocarbons and a liquid bottoms stream consisting essentially of heavy hydrocarbons;

(c) feeding the bottoms stream from the ethylene distillation column to the absorber stripper as the absorption solvent in step (a). The absorption solvent, which consists essentially of heavy hydrocarbons, is derived from the feed off-gas, thereby eliminating the need for an external solvent.

Preferentially, absorber stripping section is reboiled and, optionally, interreboiled to strip methane and hydrogen out of the heavy hydrocarbon absorber bottoms stream. Also, optionally, to increase absorption efficiency, the absorption section can be intercooled at one or more points to mitigate the rise in temperature of the solvent in the tower due to release of heat of absorption as ethylene and heavy hydrocarbons condense into the solvent.

Other significant aspects of the process of the present invention include the techniques for controlling inventory and composition of the heavy hydrocarbon absorption solvent.

Embodiments of the process of the present invention recover ethylene and associated hydrogen cost competitively with purchased ethylene and hydrogen. Moreover, the process of the present invention flexibly adapts to variations in the rate and composition typical of refining and petrochemical off-gas streams. Accordingly, the process of the present invention offers a practical, operable and cost effective technology for recovering ethylene and hydrogen that with currently available cryogenic technology is wasted.

The preceding and other features, aspects and advantages of the present invention will become apparent from the following description, appended claims, and accompanying drawings.

In the interest of clarity, pumps, heat exchangers, control valves, control systems, and auxiliary equipment items that are necessary for the practical and safe operation of the unit have intentionally been left out of the drawings if not required to elucidate the inventive concept. Skilled artisans generally understand that the deleted equipment must be included in an operating unit. It is not intended that the deletions limit the scope of the invention.

DETAILED DESCRIPTION OF THE PREFERRED EMBODIMENTS

Figure 1:
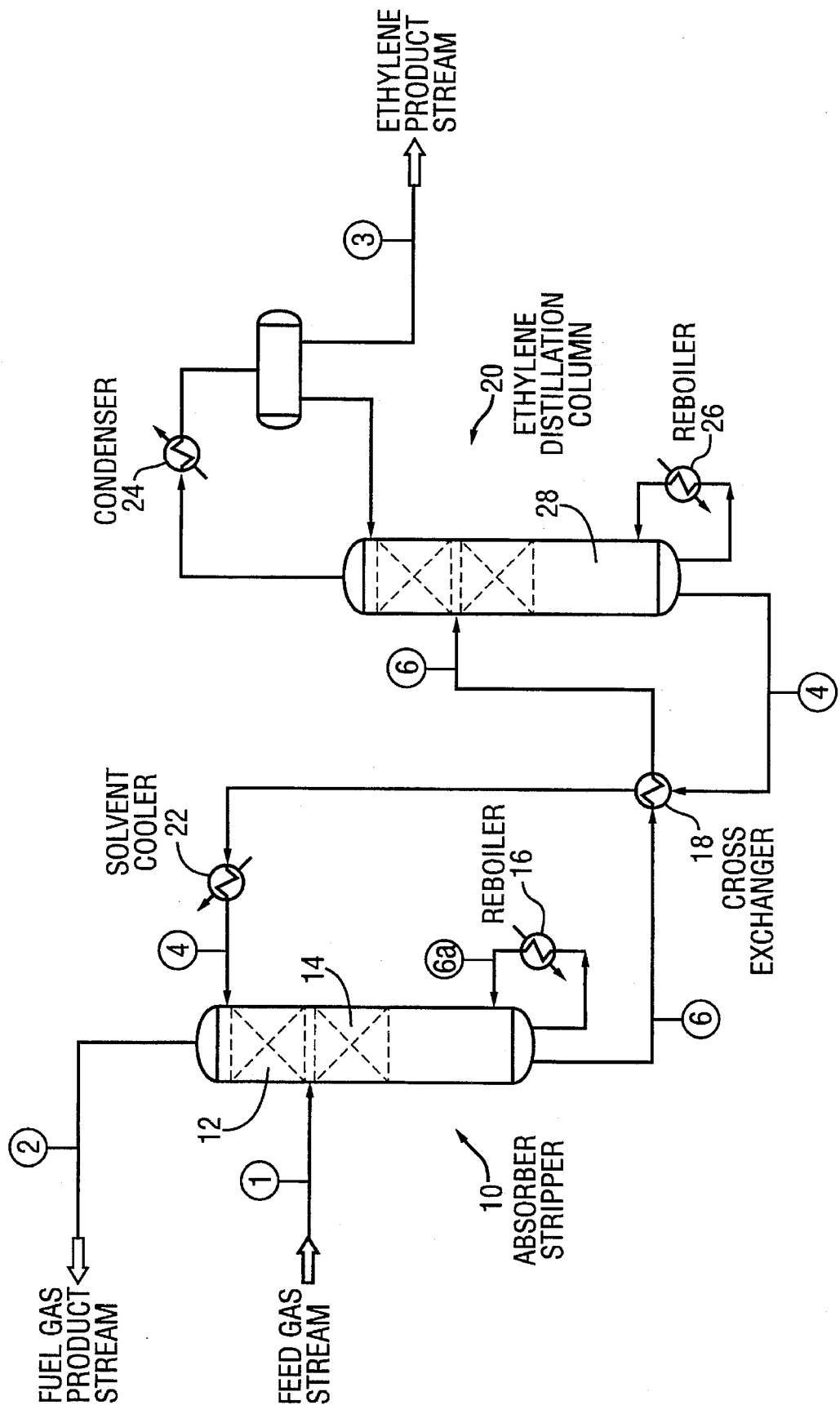
FIGS. 1 & 2 are simplified process flow diagrams of embodiments of the present invention that recover ethylene from off-gas streams wherein associated hydrogen in the feed is recovered along with methane in a fuel gas product stream produced in the process.

The following description refers to FIG. 1. The refinery and petrochemical off-gas streams that are the feed streams to the process of this invention typically contain hydrogen, methane and ethylene in various ratios and combinations. The feed gas streams also typically contain hydrocarbons heavier than ethylene which can include paraffins, olefins, naphthenes and aromatics.

The feed gas stream preferably has been treated by well known conventional means to remove water, sulfide compounds, and hydrogenated to convert acetylenes and diolefins to olefins. Water forms solid hydrates with hydrocarbons at temperatures encountered in the present process which may plug lines and equipment. Diolefins and acetylenes form oligomers which can also plug and foul lines and equipment. Accordingly, the feed stream is dried to a water dew point which is sufficiently low to preclude formation of solid hydrocarbon hydrates in the process, in the range of about −150° F. to about 10° F. Dew points in this range can be readily achieved with conventional drying units such as a molecular sieve or a glycol injection drying units.

The feed gas stream is cooled to a temperature in the range of from about 10° F. to about −50° F. (in heat exchangers not shown on FIG. 1) first by heat exchange against cold product streams leaving the process followed by cooling against a refrigerant.

The feed gas stream 1 is fed into an absorber stripper 10 at a suitable point in the midsection of the tower and flows up the column. The section of the absorber stripper 10 above the feed point is termed the "absorption section" 12 and the section below the feed point is termed the "stripping section" 14. A hydrocarbon absorption solvent stream 4 is pumped into the absorber 10 near the top of the absorber column and flows down the absorption section 12 countercurrently contacting the rising gas stream. In the absorption section 12, ethylene and heavy hydrocarbons are absorbed out of the gas stream 1 and into the solvent stream. The absorber stripper overhead gas stream 2 leaving from the top of the absorption section 12 contains most of the methane and hydrogen that came in with the feed stream. The absorber stripper overhead stream 2 is typically fed into a fuel gas system for consumption as fuel. Alternatively, the stream may be sent on to a downstream unit for further processing to separate hydrogen from methane and purify the hydrogen.

Optionally, one or more sidestreams of solvent are removed from the absorption section 12 (not shown in FIG. 1). The sidestreams are cooled in intercoolers and injected back into the absorption section at a point below the point where the stream was withdrawn. Intercooling mitigates the temperature rise of the solvent that occurs with release of the heat of absorption from condensing ethylene and higher hydrocarbons into the solvent. Intercooling improves the absorption effectiveness of the tower because the absorption capacity of the solvent decreases as the solvent temperature rises.

Solvent flows from down out of the absorption section 12 and into and down the stripping section 14 of the absorber stripper 10. The solvent stream descending into the stripping section from the absorption section unavoidably contains some hydrogen and methane that were absorbed from the feed in the absorption section. It is preferable that hydrogen and methane be stripped out of absorber stripper bottoms stream 6 before exiting the absorber stripper 10 since residual light components remain in the ethylene product stream and are more difficult and expensive to separate from ethylene. In preferred embodiments, the hydrogen and methane in the rich solvent is stripped out of the bottoms stream using a stripping gas generated by vaporizing part of the absorber stripper bottoms stream in a reboiler 16 and feeding the reboiled vapor 6a back into the bottom of the absorber stripper 10. Optionally, in addition to the reboiler, one or more solvent sidestreams (not shown in FIG. 1) can be drawn from the stripping section and vaporized in interreboilers to produce additional stripping gas which is fed into the absorber stripper at a point above the point where the stream was withdrawn. The stripping action is accomplished by the countercurrent contact between the solvent as it cascades down the stripping section and the stripping gas stream that flows up the column. Accordingly, the absorber stripper bottoms stream 6 is composed essentially of heavy hydrocarbons and absorbed ethylene.

It is important to cost effectively minimize the amount of ethylene lost in the absorber stripper overhead gas stream both to increase ethylene recovery and preclude depletion of heavy components from the system. Measures which can be taken in the design phase that improve absorption of ethylene include providing more mass transfer stages—more mass transfer surface area and height, higher efficiency packing or trays, and adding intercoolers to the absorption section. Operating measures that can be taken to increase ethylene absorption include increasing solvent circulation rate relative to gas feed rate, reducing the temperature of the solvent stream going to the tower and reducing the temperature of intercooled solvent. These measures raise investment and operating costs, so there is an economic trade-off between minimizing overhead ethylene and heavy hydrocarbon losses and controlling costs which is amenable to optimization.

The temperature in the absorption section 12 is advantageously maintained as low as practicable—refrigeration power consumption increases sharply with decreasing temperature—to reduce ethylene and solvent losses in the overhead gas stream, typically in the range of from about 30° F. to about −60° F. and preferably in the range of from about −15° F. to about −50° F. Temperature in the absorption section 12 is controlled by cooling the lean solvent entering the absorber to a controlled temperature in a solvent cooler by heat exchange against an appropriate refrigerant such as propane or propylene. As previously discussed, the temperature rise in the absorption section may be mitigated by using an intercooler.

Pressure in absorber stripper 10 is maintained in the range from about 75 psia to about 600 psia, preferably between about 150 psia and about 450 psia by controlling the back pressure of the overhead gas stream leaving from the top of the absorber stripper, using a back pressure regulating control valve. Generally, increasing tower pressure reduces the solvent recirculation rate required to achieve effective ethylene absorption but at the cost of higher power consumption.

Typically, the pressure in the absorber stripper 10 is higher than the pressure of the fuel gas system receiving the absorber stripper overhead gas stream 2. The pressure of the absorber stripper overhead gas stream 2 is reduced from absorber stripper pressure to fuel gas line pressure across a control valve, or alternatively through an expander that recovers shaft power from the expanding gas (not shown in FIG. 1). The temperature of the absorber stripper overhead gas stream drops sharply as its pressure is reduced to discharge line pressure due to the Joule Thompson effect across a control valve. Pressure letdown is controlled so as not to chill the gases below about −238° F. Residual heavy hydrocarbons in the absorber stripper overhead stream condense out of the absorber overhead gas stream as temperature declines during the pressure reduction. Condensed heavy hydrocarbons are separated from the absorber overhead gas in a separator drum recycled back into the process at a convenient point in the process (not shown in FIG. 1).

The absorber stripper tower 10 can be packed with an appropriate mass transfer packing material such as but not limited to Raschig or saddle rings. Alternatively, the absorber stripper 10 can be equipped with appropriate distillation trays such as but not limited to bubble cap, sieve tray, valve or multi-downcomer trays.

The absorber stripper bottoms stream 6, comprised of ethylene and heavy hydrocarbons, is conveyed to the ethylene distillation column 20. On its way to the ethylene distillation column 20, the absorber stripper bottoms stream 6 is heated in the cross exchanger 18 by heat exchange against the bottoms stream 4 coming from the ethylene distillation column 20. The ethylene distillation column 20 fractionates the stream 6 into an overhead stream 3 containing ethylene and heavy hydrocarbons, termed the "ethylene product stream," and a bottoms stream 4 that consists essentially of heavy hydrocarbons. The bottoms stream 4 from the ethylene distillation tower 20 is the heavy hydrocarbon absorption solvent that is pumped into the top of the absorber stripper 10. The ethylene distillation column bottoms stream 4 is cooled in the cross heat exchanger 18 against the absorber bottoms stream 6 going to the ethylene distillation tower 20. The stream 4 is cooled further by heat exchange against a refrigerant in a solvent cooler 22. The cooled stream 4 is fed into the top of the absorber 10 where it functions as the absorption solvent. A key facet of the present invention is that the heavy hydrocarbons in the solvent 4 are derived from the feed 1. The ethylene product stream 3 is sent on to other downstream units which separate and recover ethylene and other valuable heavy hydrocarbon components.

The ethylene distillation column 20 is typically of conventional design, including a reflux condenser 24 and a reboiler 26, and its internals are typically distillation trays such as bubblecap or sieve trays but can also be a suitable mass transfer packing such as Raschig or saddle rings. Optionally (not shown in FIG. 1) the ethylene distillation column can be equipped with one or more intercoolers and interreboilers.

Reflux for the ethylene distillation column is provided by an overhead condenser 24, which can be a partial or a total condenser. If the condenser is a total condenser 24 (as shown in FIG. 1), part of the condensate is fed back into the top of the tower as reflux and part of the condensate is taken off as the ethylene product stream 3. If the condenser is a partial condenser then the vapor and condensate effluent are separated in a separation drum, the condensate is fed back into the top of the tower as the reflux, and the vapor stream is the ethylene product stream.

The ethylene distillation tower is reboiled by vaporizing part of the bottoms stream in reboiler heat exchanger 26 and feeding the vapor into the bottom of the tower 20. The reboiler can be a conventional heat exchanger such as thermosyphon reboiler, a multi-pass shell and tube heat exchanger or G-fin exchanger and can be heated by steam or other heat exchange fluid medium.

The ethylene distillation column bottoms stream 4 is comprised of heavy hydrocarbons from the initial feed 1. Typically, feed heavy hydrocarbons are C4 to C10 paraffins, naphthenes, olefins, aromatics or mixtures thereof and are therefore desirable absorption solvents, as taught by Mehra.

Ethylene distillation column bottoms 4 are accumulated in an accumulation zone 28 in the bottom of the column or in a drum external to the column. The accumulation zone 28 serves as the storage reservoir for the heavy hydrocarbon solvent. The liquid level in the bottoms accumulation zone 28 is continually monitored to ensure that an adequate inventory of solvent is maintained. If it is observed that the level in the accumulation zone 28 has fallen below set point level it means that rate of flow of heavy components out of the unit in product streams, principally in the overhead stream from the ethylene distillation column, exceeds the rate of flow of heavy components in the feed stream. Accordingly, the ethylene distillation column reflux ratio is increased to drive more heavy components down the column and into the bottoms. Alternatively or additionally, the temperature in the bottom of the ethylene distillation column 20 is reduced to decrease the reboil rate which reduces the amount of heavy hydrocarbons lost in the tower overhead and increases bottoms inventory.

If it is observed that the level of bottoms 6 in the accumulation zone 28 exceeds the setpoint level it means that rate of flow of heavy components out of the unit in product streams, principally in the overhead stream 3 from the ethylene distillation column 20, is less than the rate of flow of heavy components in the feed stream. The ethylene distillation column reflux ratio is decreased, which allows more of the heavy components to escape in the tower overhead stream. Alternatively or additionally, temperature in the bottom of the ethylene distillation column is increased to increase the reboil rate which also allows more heavy hydrocarbons to escape in the ethylene distillation tower overhead stream and thus reduces solvent inventory in the accumulation zone. The bottoms temperature is increased by increasing reboil rate. Reboil rate is increased by increasing the flow of heating medium to the reboiler or, if using steam as the heating medium, increasing the steam pressure in the reboiler steam chest.

While maintaining inventory of bottoms in the accumulation zone 28 in the specified range, it is also possible to independently adjust the average carbon number of the bottoms stream within the range of carbon numbers of the heavy components in the feed by adjusting the reboil rate and the reflux rate. Increasing the reboil rate increases the average carbon number of the bottoms stream and decreasing the reboil rate decreases the carbon number of the bottoms stream. Increasing the reflux rate decreases the average carbon number of the bottoms and reducing the reflux rate increases the average carbon number of the bottoms. Generally, absorption efficiency increases with decreasing average solvent carbon number. In general, there is a functional relationship between the average carbon number of the bottoms stream and the bottoms temperature: bottoms temperature increases with increasing average carbon number of the bottoms stream. Accordingly, once having established the carbon number vs. bottoms temperature function at the column operating pressure, the average carbon number of the bottoms stream can be conveniently monitored and controlled using bottoms temperature as a control surrogate for the desired average molecular weight.

The pressure in the ethylene distillation column 20 is an independently controllable operating parameter. It is used to adjust the temperature of the bottoms stream: bottoms stream temperature increases with increasing pressure in the column. The selection of column pressure is also determined by the nature of available cooling medium such as cooling water or refrigerant for condenser 24.

Figure 2:
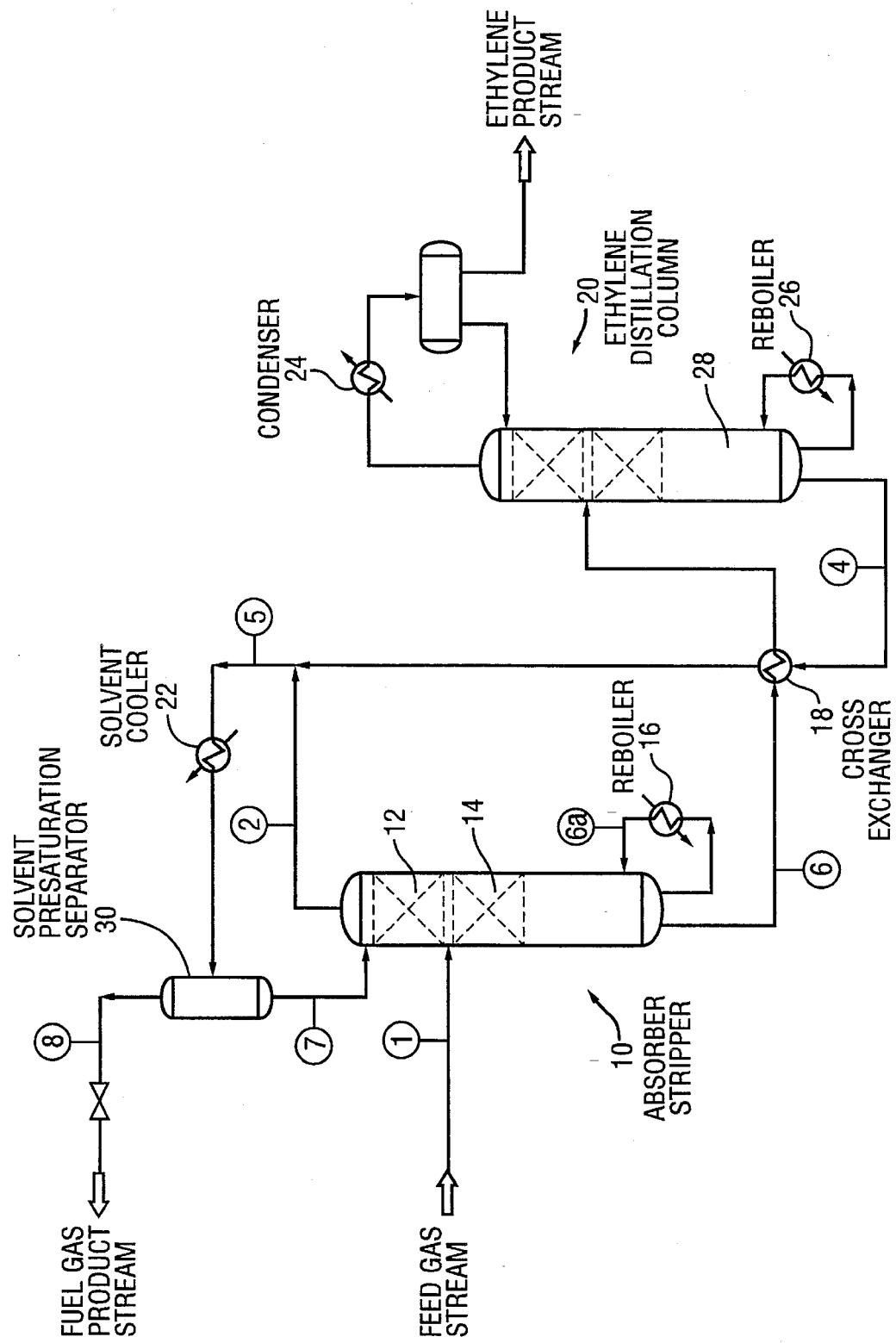

FIG. 2 presents an alternative embodiment of the process of this invention wherein hydrogen in the feed off-gas is recovered in the fuel product stream together with methane. In the process of FIG. 2, the bottoms stream 4 from the ethylene distillation column 20 rather than flowing directly to the top of the absorber stripper 10 as in the process of FIG. 1, is combined with the overhead gas stream 2 from absorber stripper 10. The combined stream 5 is cooled in a solvent cooler 22 using a refrigerant as the cooling medium. The combined stream 5 is conveyed into a solvent presaturation separator 30 which produces an overhead gas stream 8 which is the fuel gas product stream comprising methane and hydrogen, and a bottoms liquid stream 7 which is comprised of heavy hydrocarbons presaturated with hydrogen and methane. The presaturated heavy hydrocarbon stream 7 is fed into the top of the absorber stripper 10 where it functions as the absorption solvent. Presaturating the heavy hydrocarbon solvent with hydrogen and methane increases absorption of ethylene and heavier hydrocarbons in the absorber stripper 10 and reduces the amount of ethylene and higher hydrocarbons lost in the fuel gas product stream 8.

From the preceding discussion it is now apparent that in the embodiments of the process of this invention of FIGS. 1 and 2, the absorber stripper absorption solvent is produced in the ethylene distillation column from heavy components in the feed as the bottoms stream from the ethylene distillation column 20. As taught by Mehra, the absorption solvent is preferably a mixture of hydrocarbon with average carbon number in the range of from C4 to C10 including paraffins, olefins, naphthenes and aromatics. Specifically avoided are diolefins and acetylene because these compounds have propensity to oligomerize and concentrate in the towers and foul and plug the equipment. It is good practice to periodically or continuously purge a small fraction of the ethylene distillation column bottoms stream to prevent buildup of hydrocarbon oligomers. The average carbon number of the solvent can be controlled within the range of carbon numbers of the heavy components of the feed gas by adjusting the reboil rate of the column.

In the embodiments of FIGS. 1 and 2, hydrogen leaves the process in the absorber stripper overhead along with methane as the fuel gas product stream 2. In the two alternate embodiments of the process of the present invention that follow, additional operations are added to the process to recover hydrogen in a separate "hydrogen product stream." The recovered hydrogen can be readily purified by well known techniques such as pressure swing adsorption (PSA) for use in chemical applications where high purity (99.999 mol %) hydrogen is desired.

Figure 3:
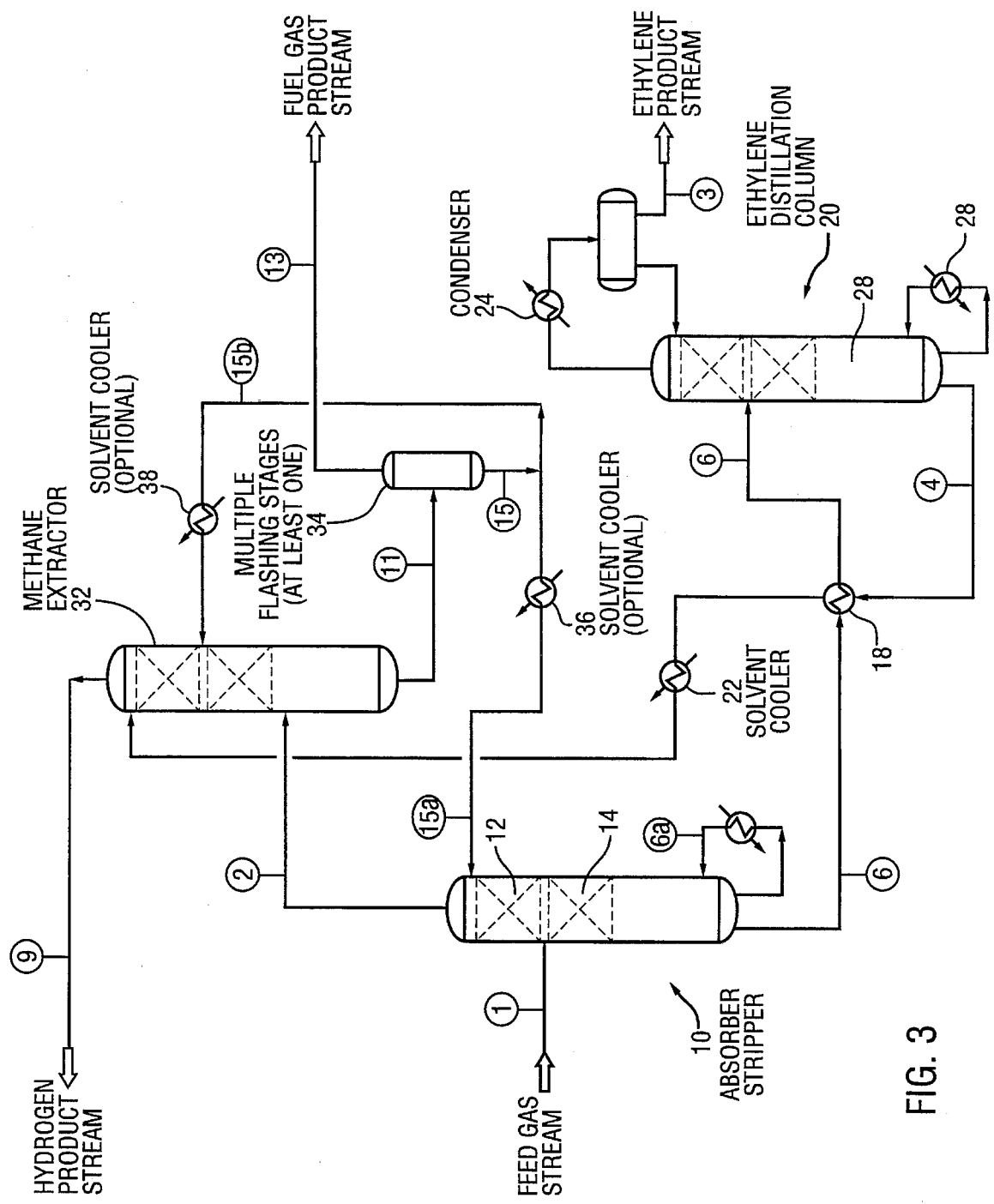
FIGS. 3 and 4 are simplified process flow diagrams of embodiments of the present invention that recover ethylene wherein hydrogen is recovered in a separate hydrogen product stream apart from the fuel gas product stream.

FIG. 3 is a simplified process flow diagram depicting an embodiment of the present invention in which hydrogen and methane are recovered separately in different product streams. In the embodiment of FIG. 3, the absorber and the ethylene distillation column operate as described previously in the discussion of the processes of FIGS. 1 and 2.

The absorber stripper overhead gas stream 2, which is comprised of methane and hydrogen, is fed into the bottom of the methane extractor 32. The methane extractor internals can be either packing or trays. The bottoms stream 4 from the ethylene distillation column 20 which consists essentially of heavy hydrocarbons derived from the feed stream is fed into the top of the methane extractor 32. There the rising gas stream countercurrently contacts the ethylene distillation column bottoms stream as it cascades down the extractor. The ethylene distillation bottoms stream 4 absorbs methane out of the methane/hydrogen coming overhead from the absorber stripper 2 to produce a methane extractor overhead gas stream 9 consisting essentially of hydrogen, the "hydrogen product stream 9." The hydrogen product stream 9 can be purified in a downstream unit to meet chemical specifications.

The bottoms stream from the methane extractor 11 is comprised of heavy hydrocarbons and absorbed methane. The methane is flashed out of the heavy hydrocarbons in one or more flash drums 34 in series. The flash drums are connected so the liquid stream can flow in series from the upstream flash drum, through the intermediate flash drums and into the downstream flash drum. Pressure decreases moving from the upstream flash drum to the downstream flash drum.

The overhead flash gas streams 13 from the flash drums are comprised of methane. They are combined to form the fuel gas product stream, which typically is a suitable fuel gas.

The bottoms liquid stream 15 drawn from the downstream flash drum 34 is divided into two parts: One part is fed into the top of the absorber stripper as the absorption solvent 15a for the absorber stripper 10; this stream may be cooled in an optional solvent cooler 36 by heat exchange against a refrigerant. The other part 15b of the flash drum bottoms is fed into the methane extractor 32 as a second solvent stream at a point below the point where the ethylene distillation column bottoms stream 4 is fed into the methane extractor 32; optionally this stream may also be cooled in a cooler 38.

Figure 4:
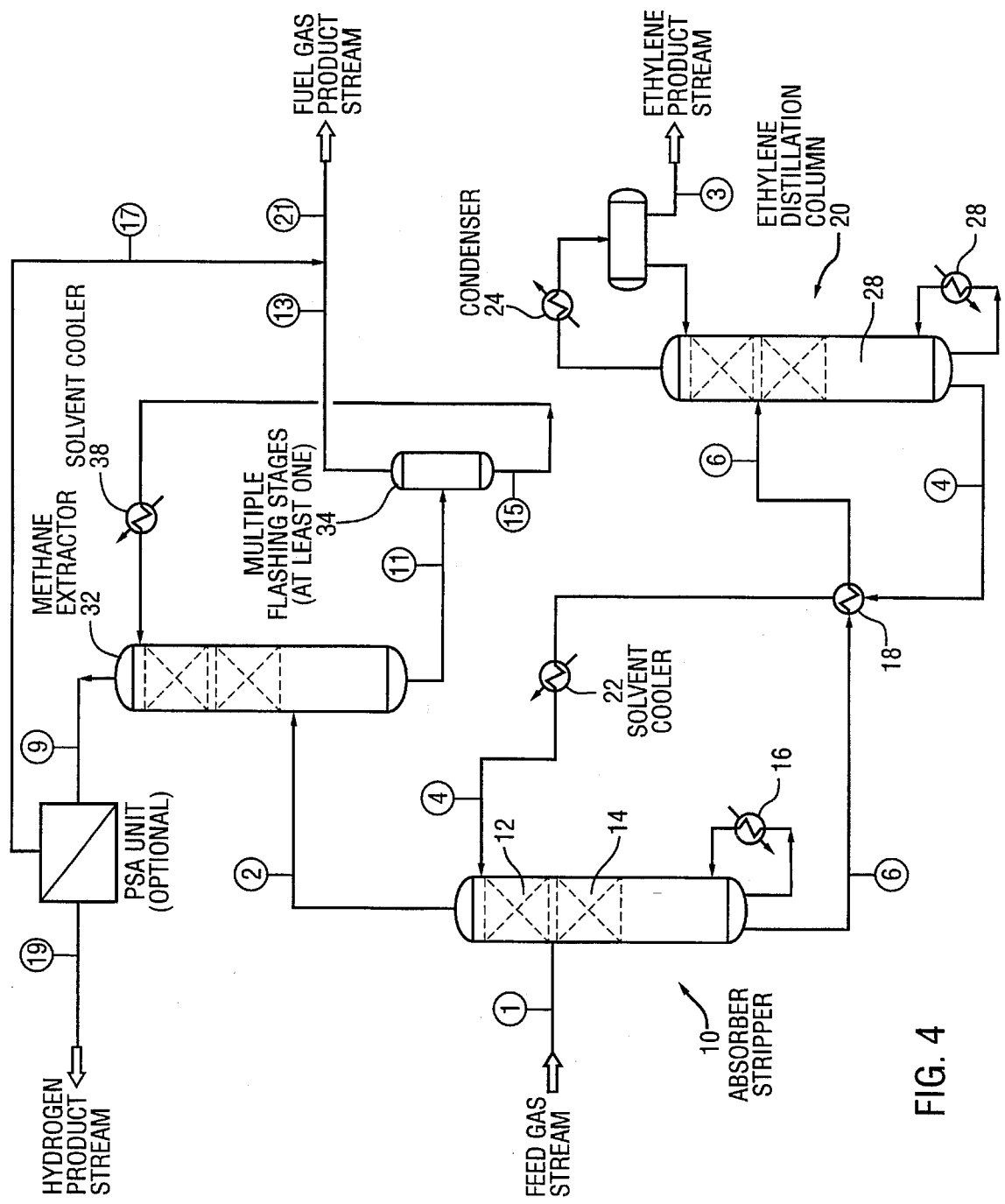

FIG. 4 is a simplified process flow diagram depicting another embodiment of the process of this invention wherein hydrogen and methane are recovered in separate product streams. As in the process of FIG. 3, a methane extractor 32 is used to produce an overhead hydrogen product stream 9 by absorbing methane out of the overhead gas stream 2 from the absorber stripper 10 gas stream via countercurrent contact with a stream of heavy hydrocarbons. However, in the process embodiment of FIG. 4 two different heavy hydrocarbon solvent circuits are maintained: one for the absorber stripper 10 and one for the methane extractor 32, each with different composition but both comprised of heavy hydrocarbons derived from the feed 1.

In FIG. 4 embodiment, one lean solvent loop is created by circulating the entire heavy hydrocarbon solvent stream 6 from the bottom of the absorber stripper 10, into the ethylene distillation column 20, and from the bottom 4 of the ethylene distillation column into the top of the absorber stripper 10. The second heavy hydrocarbon solvent circuit is established by conveying the lean solvent stream 15 from the downstream flash drum 34 to the top of the methane extractor 32 and from the bottom 11 of the methane extractor 32 to the upstream flash drum 34. Thus, in FIG. 4 embodiment, two independent heavy hydrocarbon solvent circulation loops are maintained producing two heavy hydrocarbon solvents with different compositions with both solvents comprising heavy components derived from the feed stream.

The advantage of the two solvent FIG. 4 embodiment relative to the one solvent FIG. 3 embodiment is that the compositions of the two solvent streams can be separately controlled to optimize methane absorption in the methane extractor and ethylene absorption in the absorber stripper.

The average carbon number of the heavy hydrocarbon stream from the downstream flash drum is controlled within the range of hydrocarbons in the feed gas by controlling the pressure in the flash drums; reducing flash drum pressure increases average carbon number of the solvent.

FIG. 4 includes an optional PSA unit 40 that purifies the hydrogen product stream 9 coming overhead from the methane extractor 32. The PSA unit produces a purge stream 17 containing impurities removed from the hydrogen product stream 19. The reject stream 17 is rich in methane and accordingly is added to the fuel gas stream 13 coming overhead from the flash drums 34 to form the fuel gas product stream 21.

When initially starting up the process of this invention, there is of course no heavy hydrocarbon solvent inventory in the flash drums or in the ethylene distillation column bottoms accumulation zone. The required inventories of heavy hydrocarbons can be accumulated from the feed stream by operating the unit with no bottoms flow from the flash drum and the ethylene distillation column accumulation zone until heavy hydrocarbon solvent inventories reach the set point values. The composition of the solvent inventories will, in a few hours, equilibrate to their steady state compositions.

The processes of the present invention depicted in FIGS. 3 and 4 recover ethylene, hydrogen, methane and heavy hydrocarbons from petrochemical and refinery off-gas streams via physical absorption using solvents comprised of heavy hydrocarbons that are derived from the feed and produced within the process; no external solvent is used.

In conventional absorption processes, the solvent is an external solvent that is purchased and stored in a tank near the absorber stripper. Periodically or continually, solvent is pumped from the storage tank to the absorber stripper to makeup losses of solvent. The process of this invention does not use an external solvent, but instead produces the solvent from heavy components in the feed stream. Accordingly, there is no need to purchase, store and handle external solvent. This results in significant reduction in investment and operating costs relative to processes that use external solvents.

The process of the present invention sufficiently is cost competitive, flexible, and safe to induce operators to recover ethylene and hydrogen from refining and petrochemical off-gas rather than to burn them in flares or consume them as relatively low value fuel gas. Clearly, the prospects for penetration and acceptance of absorption processes for recovering ethylene and associated hydrogen from refinery and petrochemical off-gas streams are enhanced by the improvements encompassed in the process of the present invention.

EXAMPLE I

Table 2 below presents a heat and material balance for the process of FIG. 1 including flow rate, composition, temperature and pressure for key process streams that are indicated on FIG. 1.

TABLE 2

| Stream* Component | 1 lb-mol/hr | 2 lb-mol/hr | 3 lb-mol/hr | 4 lb-mol/hr |
|---|---|---|---|---|
| Hydrogen | 1,923.70 | 1,923.70 | 0.00 | 0.00 |
| Nitrogen | 168.57 | 168.57 | 0.00 | 0.00 |
| CO | 43.14 | 43.14 | 0.00 | 0.00 |
| Methane | 3,934.38 | 3,932.98 | 1.40 | 0.00 |

TABLE 2-continued

| Stream* Component | 1 lb-mol/hr | 2 lb-mol/hr | 3 lb-mol/hr | 4 lb-mol/hr |
|---|---|---|---|---|
| Ethylene | 843.13 | 43.43 | 799.70 | 0.03 |
| Ethane | 1,597.61 | 0.53 | 1,597.08 | 0.36 |
| Propylene | 125.43 | 0.23 | 125.20 | 2.70 |
| Propane | 122.32 | 0.36 | 121.96 | 5.30 |
| n-Butane | 195.52 | 3.93 | 191.59 | 288.61 |
| n-Pentane | 72.48 | 13.27 | 59.21 | 4,653.00 |
| Total | 9,026.28 | 6,130.14 | 2,896.14 | 4,950.00 |
| Temperature, °F. | 100 | −32 | 100 | −40 |
| Pressure, psia | 580 | 540 | 285 | 550 |

*Stream Numbers Refer to FIG. 1

The heat and material balance was computed using a commercial process simulation computer program widely used to design process plants. The feed gas stream (Stream No. 1) is a representative refinery off-gas stream. It contains hydrogen, methane and ethylene. The heavy hydrocarbons in the feed stream are n-butane and n-pentane. In accordance with the present invention, the bottoms stream from the ethylene distillation column (Stream No. 4), which is the absorption solvent, is comprised essentially of the heavy hydrocarbons from the feed stream, n-butane and n-pentane. About 95% of the ethylene in the feed is recovered in the ethylene product stream (Stream No. 3). Essentially all of the hydrogen and methane in the feed stream are recovered together in the fuel gas stream, the overhead gas stream from the absorber stripper (Stream No. 2).

The heavy components that come into the process in the feed (195.52 lb mols per hour of butane and 72.48 lb. mols per hour of pentane) leave the process distributed between the fuel gas product stream (3.93 lb mols per hour of butane and 13.37 lb mols per hour of pentane) and the ethylene product stream (191.59 lb mols per hour of butane and 59.21 lb mols per hour of pentane).

EXAMPLE II

Table 3 below presents a heat and material balance for the process of FIG. 4 including flow rate, composition, temperature and pressure for key process streams that are indicated on FIG. 4.

gen, methane and ethylene. The heavy hydrocarbon components in the feed stream are n-butane and n-pentane. In accordance with the present invention, the bottoms stream from the ethylene distillation column (Stream No. 4) and flash drum bottoms stream (Stream No. 15), which are the two heavy hydrocarbon absorption solvent streams, are comprised of the heavy hydrocarbons in the feed, n-butane and n-pentane. The two heavy hydrocarbon solvent streams have different compositions: the solvent stream to the stripper absorber (Stream No. 4 is comprised of about 4.7 mol % n-butane and 95 mol % n-pentane; the solvent stream 15 to the methane absorber is comprised of about 2.3 mol % n-butane and 96.1 mol % of n-pentane.

In the process of FIG. 4, 93% of the hydrogen in the feed is recovered in the overhead gas stream from the methane extractor (Stream No. 9), and essentially all of the methane in the feed stream is recovered separately in the overhead stream from the flash drums (Stream No. 21). Ninety-five percent of the ethylene in the feed stream is recovered in the ethylene product stream (Stream No. 3).

The overhead gas stream from the methane extractor (Stream No. 9) is sent on to a PSA unit in which the hydrogen is concentrated and purified to form the hydrogen product stream (Stream No. 19).

The purge stream 17 from the PSA contains methane. It is combined with the overhead stream from the flash drums (Stream No. 13) to form the fuel gas product stream (Stream No. 21).

The heavy hydrocarbons that come into the process in the feed (Stream No. 1) leave the process distributed between the ethylene product stream (Stream No. 3) and the fuel gas product stream (Stream No. 21).

Although the present invention has been described in considerable detail with reference to the preferred embodiments discussed, other embodiments are possible and are readily understood by those skilled in the process engineering arts. Therefore, the spirit and scope of the appended claims are not limited to the specific preferred process embodiments described herein.

What is claimed is:

1. A continuous process for recovering ethylene from a feed gas stream that is comprised of ethylene, methane and heavy hydrocarbons, the process comprising the steps of:

introducing the feed gas stream, in the absence of an external absorption solvent, to an absorber stripper;

TABLE 3

| Stream* Component | 1 lb-mol/hr | 3 lb-mol/hr | 4 lb-mol/hr | 2 lb-mol/hr | 9 lb-mol/hr | 13 lb-mol/hr | 19 lb-mol/hr | 21 lb-mol/hr | 15 lb-mol/hr |
|---|---|---|---|---|---|---|---|---|---|
| Hydrogen | 1,914.34 | 0.00 | 0.00 | 1,914.34 | 1,782.43 | 131.91 | 1,515.00 | 399.34 | 0.05 |
| Nitrogen | 365.43 | 0.00 | 0.00 | 365.43 | 278.87 | 86.56 | 0.00 | 365.43 | 0.44 |
| CO | 50.74 | 0.00 | 0.00 | 50.74 | 34.82 | 15.92 | 0.00 | 50.74 | 0.14 |
| Methane | 3,731.71 | 1.38 | 0.00 | 3,730.33 | 448.88 | 3,281.45 | 0.00 | 3,730.33 | 269.33 |
| Ethylene | 830.20 | 789.00 | 0.03 | 41.20 | 3.07 | 38.13 | 0.00 | 41.20 | 39.64 |
| Ethane | 1,583.35 | 1,582.81 | 0.34 | 0.54 | 0.04 | 0.50 | 0.00 | 0.54 | 0.99 |
| Propylene | 295.87 | 295.33 | 6.44 | 0.54 | 0.05 | 0.49 | 0.00 | 0.54 | 5.47 |
| Propane | 221.21 | 220.54 | 9.77 | 0.67 | 0.00 | 0.61 | 0.00 | 0.67 | 8.58 |
| n-Butane | 112.60 | 106.89 | 232.03 | 5.71 | 0.60 | 5.11 | 0.00 | 5.71 | 446.04 |
| n-Pentane | 37.86 | 27.39 | 4,701.38 | 10.47 | 4.87 | 5.60 | 0.00 | 10.47 | 18,785.80 |
| Total | 9,143.31 | 3,023.34 | 4,949.99 | 6,119.97 | 2,553.69 | 3,566.28 | 1,515.00 | 4,604.97 | 19,555.48 |
| Temperature, °F. | 55 | 50 | −40 | −32 | −23 | 100 | 95 | 100 | −25 |
| Pressure, psia | 557 | 240 | 545 | 540 | 525 | 75 | 51 | 75 | 530 |

*Stream Numbers Refer to FIG. 4

The heat and material balance was computed using a commercial process simulation computer program widely used to design process plants. The feed gas stream (Stream No. 1) is a representative refinery off-gas stream. It contains hydrocontacting the feed gas stream with an absorption solvent stream comprised of heavy hydrocarbons in the absorber stripper, wherein the section of the absorber stripper above the feed point is the absorption section and the section of the absorber stripper below the feed point is the stripping section, to produce an absorber stripper overhead gas stream comprised of methane and an absorber stripper bottoms stream comprised of the heavy hydrocarbons and ethylene;

fractioning the absorber stripper bottoms stream in an ethylene distillation column to produce an overhead stream comprising ethylene and heavy hydrocarbons that is the ethylene product stream, and a liquid bottoms stream comprising heavy hydrocarbons that are derived from the feed gas stream;

adjusting the reflux and reboil rates of the ethylene distillation column to control the bottoms inventory within a specified range;

feeding the liquid bottoms steam from the ethylene distillation column to the absorber stripper as the absorption solvent stream; and adjusting the flow rate of the liquid bottoms stream from the ethylene distillation column to the absorber stripper to control the concentration of ethylene and heavy hydrocarbons in the absorber overhead gas stream within a specified range.

2. The process of claim 1 wherein the feed gas stream and the absorber stripper overhead gas stream also comprises hydrogen.

3. The process of claim 1 comprising the additional step of: reboiling the absorber stripper bottoms stream so as to strip away hydrogen and methane.

4. The process of claim 1 comprising the additional step of: intercooling the absorption section of the absorber stripper.

5. The process of claim 1 wherein the average carbon number of the ethylene distillation column bottoms is maintained in a specified range.

6. The process of claim 1 wherein the feed gas is essentially devoid of acetylenes, dienes, water, and sulfur compounds.

7. The process of claim 1 comprising the additional steps of:

depressing the absorber stripper overhead gas stream across an expansion device wherein the temperature of the stream is decreased forming condensate; and separating the condensate from the cooled absorber stripper overhead gas stream and conveying the condensate to the absorber stripper or ethylene distillation column.

8. A continuous process for recovering ethylene from a feed gas stream that is comprised of ethylene, methane and heavier hydrocarbons, the process comprising the steps of:

introducing the feed gas stream, in the absence of an external absorption solvent, to an absorber stripper;

contacting the feed gas stream with a presaturated heavy hydrocarbon stream in an absorber stripper, wherein the section of the absorber stripper above the feed point is the absorption section and the section of the absorber stripper below the feed point is the stripping section, to produce an absorber overhead gas stream comprised of methane and a rich solvent absorber stripper bottoms stream comprised of ethylene and heavier hydrocarbons;

fractionating the rich solvent absorber stripper bottoms stream in an ethylene distillation column to produce an overhead ethylene product stream comprising ethylene and heavy hydrocarbons, and a heavy hydrocarbons bottoms stream derived from the feed gas stream;

adjusting the reflux and reboil rates of the ethylene distillation column to control the bottoms inventory within a specified range;

combining the absorber overhead gas stream from the absorber stripper and the heavy hydrocarbons bottoms stream from the ethylene distillation column, cooling the combined stream in a solvent cooler and conveying the combined stream to a solvent presaturation separator to produce a fuel gas product stream comprising methane, and a presaturated heavy hydrocarbons liquid stream that is saturated with methane, and conveying the presaturated heavy hydrocarbon steam to the absorber stripper as the presaturated heavy hydrocarbon stream, and adjusting the flow rate of the heavy hydrocarbons bottoms stream from the ethylene distillation column to control the concentration of ethylene and heavy hydrocarbons in the fuel gas product stream.

9. The process of claim 8 wherein both the feed gas stream and the absorber stripper overhead stream also comprise hydrogen and wherein the presaturated heavy hydrocarbon stream is also saturated with hydrogen.

10. A continuous process for recovering ethylene and hydrogen from a feed gas stream that comprises hydrogen, methane, ethylene, and heavy hydrocarbons, the process comprising the steps of:

introducing the feed gas stream, in the absence of an external absorption solvent, to an absorber stripper;

contacting the feed gas stream with a liquid stream comprised of heavy hydrocarbons in an absorber stripper to produce an absorber stripper overhead gas stream comprising hydrogen and methane, and an absorber stripper bottoms stream comprising ethylene and heavy hydrocarbons;

feeding the absorber stripper bottoms stream to an ethylene distillation column to produce an overhead product stream comprising ethylene and heavy hydrocarbons, and a first heavy hydrocarbons bottoms stream derived from the feed;

adjusting the reflux and reboil rates of the ethylene distillation column to control the first heavy hydrocarbons bottoms inventory within a specified range;

contacting the absorber stripper overhead gas stream with the first heavy hydrocarbons bottoms stream, and also a second heavy hydrocarbon stream, in a methane extractor to produce an overhead hydrogen product stream and a methane extractor bottoms stream comprising heavy hydrocarbons and methane;

flashing the methane extractor bottoms stream in one or more stages connected in series to produce a flash overhead gas stream comprising methane that is the fuel gas product stream and a flash bottoms stream drawn from the downstream flash drum comprising heavy hydrocarbons derived from the feed;

dividing the flash drum bottoms stream into two parts and feeding one part to the absorber stripper as the heavy hydrocarbon stream and the other part to the methane extractor as the second heavy hydrocarbon stream; and adjusting the flow rate of downstream flash drum bottoms stream to the absorber stripper to control the concentration of ethylene and heavy hydrocarbons in the absorber stripper overhead gas stream within a specified range.

11. The process of claim 10 comprising the additional step of: adjusting the flow rate of both the first heavy hydrocarbons bottoms stream and the second heavy hydrocarbon stream into the methane extractor to control the methane concentration in the methane extractor overhead gas within a specified range.

12. The process of claim 10 wherein the average carbon number of the ethylene distillation bottoms is maintained in a specified range.

13. The process of claim 10 wherein the feed gas is essentially devoid of acetylenes, dienes, water, and sulfur compounds.

14. The process of claim 10 comprising the additional steps of:

conveying the overhead hydrogen product stream from the methane extractor to a hydrogen purification unit and concentrating and purifying the hydrogen product stream to produce a purified hydrogen product stream and a purge stream containing methane and other components separated from the purified hydrogen stream; and adding the purge stream into the fuel gas product stream.

15. The process of claim 10 comprising the additional step of: adjusting the pressures in the flash drums to maintain the average carbon number of the downstream flash drum bottoms within a specified range.

16. A continuous process for recovering ethylene and hydrogen from a feed gas stream that comprises hydrogen, methane, ethylene, and heavy hydrocarbons, the process comprising the steps of:

introducing the feed gas stream, in the absence of an external absorption solvent, to an absorber stripper;

contacting the feed gas stream with an absorption solvent stream comprised of heavy hydrocarbons in an absorber stripper to produce an absorber stripper overhead gas stream comprised of methane and hydrogen, and an absorber stripper bottoms stream comprised of heavy hydrocarbons and ethylene;

fractionating the absorber stripper bottoms stream in an ethylene distillation column to produce an overhead ethylene product stream comprising ethylene and heavy hydrocarbons, and a heavy hydrocarbons bottoms stream derived from the feed gas stream, which is conveyed to the absorber stripper as the absorption solvent stream;

adjusting the reflux and reboil rates of the ethylene distillation column to control the bottoms inventory within a specified range;

adjusting the flow rate of ethylene distillation column bottoms stream going into the absorber stripper to control the concentration of ethylene and heavy hydrocarbons in the absorber stripper overhead gas stream within a specified range;

contacting the absorber stripper overhead gas stream with a stream comprised of heavy hydrocarbons in a methane extractor to produce an overhead hydrogen product stream and a methane extractor bottoms stream comprising heavy hydrocarbons and methane; and flashing the methane extractor bottoms stream in one or more stages connected in series to produce flash overhead gas streams comprising methane that are combined to form a fuel gas product stream, and a flash bottoms stream drawn from the downstream flash drum comprising heavy hydrocarbons which is fed into the methane extractor.

17. The process of claim 16 comprising the additional steps of:

conveying the overhead gas stream from the methane extractor to a hydrogen purification unit and concentrating and purifying the hydrogen product stream to produce a purified hydrogen product stream and a purge stream containing methane and other components separated from the purified hydrogen stream; and adding the purge stream into the fuel gas product stream.

18. The process of claim 16 comprising the additional step of: adjusting the flow rate of the bottoms stream drawn from the downstream flash drum to the methane extractor to control the methane concentration in the methane extractor overhead gas within a specified range.

19. The process of claim 16 wherein the average carbon number of the ethylene distillation bottoms is maintained within a specified range.

20. The process of claim 16 wherein the feed gas is essentially devoid of acetylenes, dienes, water, and sulfur compounds.

21. The process of claim 16 comprising the additional step of: adjusting the pressures in the flash drums to maintain the average carbon number of the bottoms stream in the downstream flash drum within a specified range.

* * * * *

UNITED STATES PATENT AND TRADEMARK OFFICE
CERTIFICATE OF CORRECTION

PATENT NO. :   5,546,764

DATED      :   August 20, 1996

INVENTOR(S) :
    YUV R. MEHRA

It is certified that error appears in the above-indentified patent and that said Letters Patent is hereby corrected as shown below:

In column 13, line 6, please delete "fractioning" and insert therefor --fractionating--.

In column 13, line 39, please delete "depressing" and insert therefor --depressuring--.

In column 14, line 9, please delete "steam" and insert therefor --stream--.

Signed and Sealed this

Seventh Day of January, 1997

*Attest:*

BRUCE LEHMAN

*Attesting Officer*    *Commissioner of Patents and Trademarks*